United States Patent [19]
Mak

[11] Patent Number: 5,698,765
[45] Date of Patent: Dec. 16, 1997

[54] MOUSE HAVING A DISRUPTED CD4 GENE

[75] Inventor: Tak W. Mak, Toronto, Canada

[73] Assignee: The Ontario Cancer Institute, Toronto, Canada

[21] Appl. No.: 400,173

[22] Filed: Mar. 6, 1995

Related U.S. Application Data

[63] Continuation of Ser. No. 111,581, Aug. 4, 1993, abandoned, which is a continuation-in-part of Ser. No. 801,405, Dec. 2, 1991, abandoned.

[51] Int. Cl.$^6$ ..................................................... C12N 5/00
[52] U.S. Cl. .................... 800/2; 800/DIG. 1; 435/240.1
[58] Field of Search .................... 800/2, DIG. 1; 435/240.1

[56] References Cited

PUBLICATIONS

Zijlstra et al (1989) Nature 342, 435–438.
Gorman et al (1987) Proced. Natl. Acad. Sci. 84, 7644–7648.

Primary Examiner—Deborah Crouch
Attorney, Agent, or Firm—Marshall, O'Toole, Gerstein, Murray & Borun

[57] ABSTRACT

A mutant mouse strain without CD4 expression has been generated by disrupting the CD4 gene using embryonic stem cell technology. In these mice CD4$^+$ T lymphocytes are not present in peripheral lymphoid organs, but the development of CD8$^+$ T cells and myeloid components is unaltered, indicating that expression of CD4$^+$ on progenitor cells and CD4$^+$ CD8$^+$ (double positive) thymocytes is not obligatory. These mice have markedly decreased helper cell activity for antibody responses, whereas cytotoxic T cell activity against viruses was within normal range of that generated by CD4$^+$ mice. This differential requirement for CD4$^+$ helper T cells has important implications for the understanding of the immune function in a variety of immune disorders, including AIDS, in which the CD4$^+$ cells are reduced or absent.

5 Claims, 7 Drawing Sheets

MOUSE HAVING A DISRUPTED CD4 GENE

This is a continuation of U.S. application Ser. No. 08/111,581, filed Aug. 4, 1993, now abandoned, which is a continuation-in-part of U.S. application Ser. No. 07/801,405, filed Dec. 2, 1991, now abandoned.

The invention is a mutant mice lacking the CD4 surface marker on its T lymphocytes. The invention as expressed, for example, in mutant mice is useful for the study of CD4 in T cell maturation and the function of CD4$^+$ T cells in the immune system.

T cells express T cell antigen receptors (TcR) for antigen recognition. Unlike the antibody molecule, the TcR only functions in a cell associated fashion and does not recognize free antigen. Instead, T cells recognize fragments of protein antigens bound to molecules of the major histocompatibility complex (MHC) on the surface of other cells. In addition to the TcR, T cells express two key surface co-receptors, CD4 and CD8, which are involved in the interaction with their ligands. These CD4 and CD8 molecules participate in a complex series of differentiation and selection steps which thymocytes undergo during maturation in the thymus to T lymphocytes. T cells which emerge from the thymus bear either one or the other of two co-receptors. Since the CD4 molecule is expressed on the early haemopoietic progenitor as well as the early thymic precursor cells, a role for the CD4 molecule in haemopoiesis and T cell development has been implicated.

T cell precursors entering the thymus express CD4 at a low level. These cells differentiate through a stage when they express neither CD4 nor CD8 (double negative). They then express both CD4 and CD8 (double positive) and low levels of CD3 and TcR. It is at this stage of development that the T cells undergo positive or negative selection and eventually emerge as mature CD4$^+$8$^-$ or CD4$^-$8$^+$ (single positive) T cells. In general, helper T cells bear the CD4 molecule on their surfaces and recognize foreign peptides in the context of class II MHC molecules, and cytotoxic T cells express CD8 and are class I MHC restricted. The role of CD4$^+$ T cells in both B and T cell immunological responses has been studied for many years, and it has gained particular importance in the understanding of acquired immune-deficiency syndrome (AIDS), where the CD4$^+$ T cells are reduced or absent. Until recently, studies of the role of CD4$^+$ T cells in vivo have been based on adoptive transfer experiments of selected or depleted lymphocytes, or on in vivo treatment of thymectomized mice with monoclonal antibodies causing depletion of CD4$^+$ T cells[1-4]. These models, however, may be subject to various experimental and procedural limitations and do not permit the study of the role of the CD4 molecule in T cell differentiation.

A major advance in ascertaining the importance of the CD4 molecule in the development and function of T cells is provided by the present invention. To obtain a mutant mouse of the invention, the CD4 gene in embryonic mouse stem (ES) cells[5,6] were disrupted by homologous recombination[7,8]. Germ-line transmission[9,10] of the mutation has resulted in the generation of a mutant mouse strain that does not express the CD4 molecule on the cell surface.

Gene Targeting of CD4

Figure 1A:
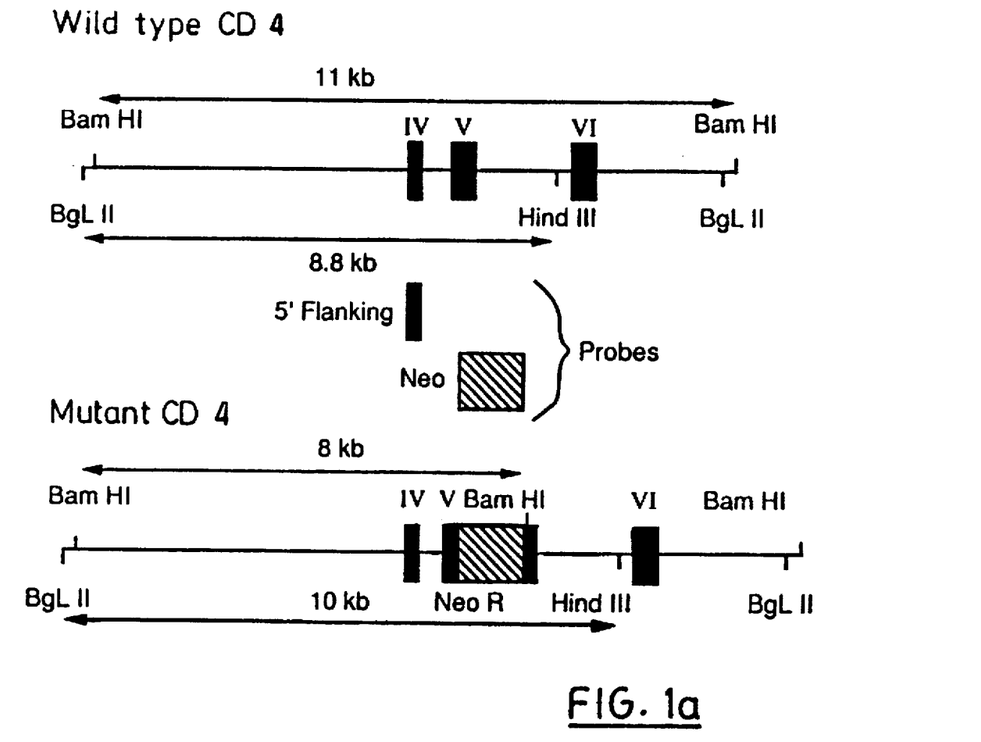
FIG. 1a shows schematic diagrams of the structure of the CD4 locus in parental D3 cells (wild type CD4), and the predicted structure of the targeted CD4 locus (mutant CD4).
Figure 1B:
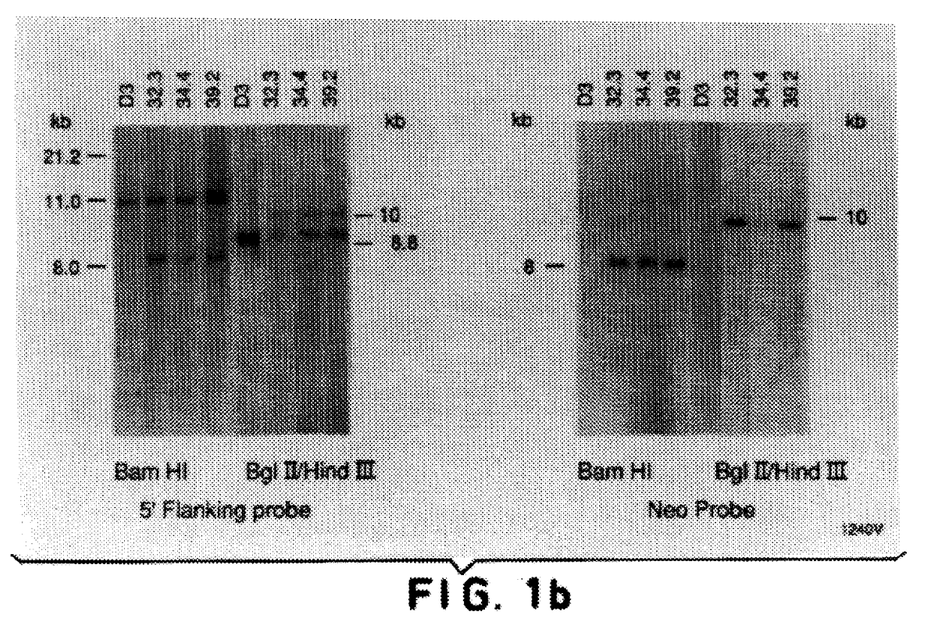
FIG. 1b shows Southern blot analyses of the structure of the CD4 locus in the DNA of parental D3 cells and three target clones 32.3, 34.4 and 39.2.
Figure 1C:
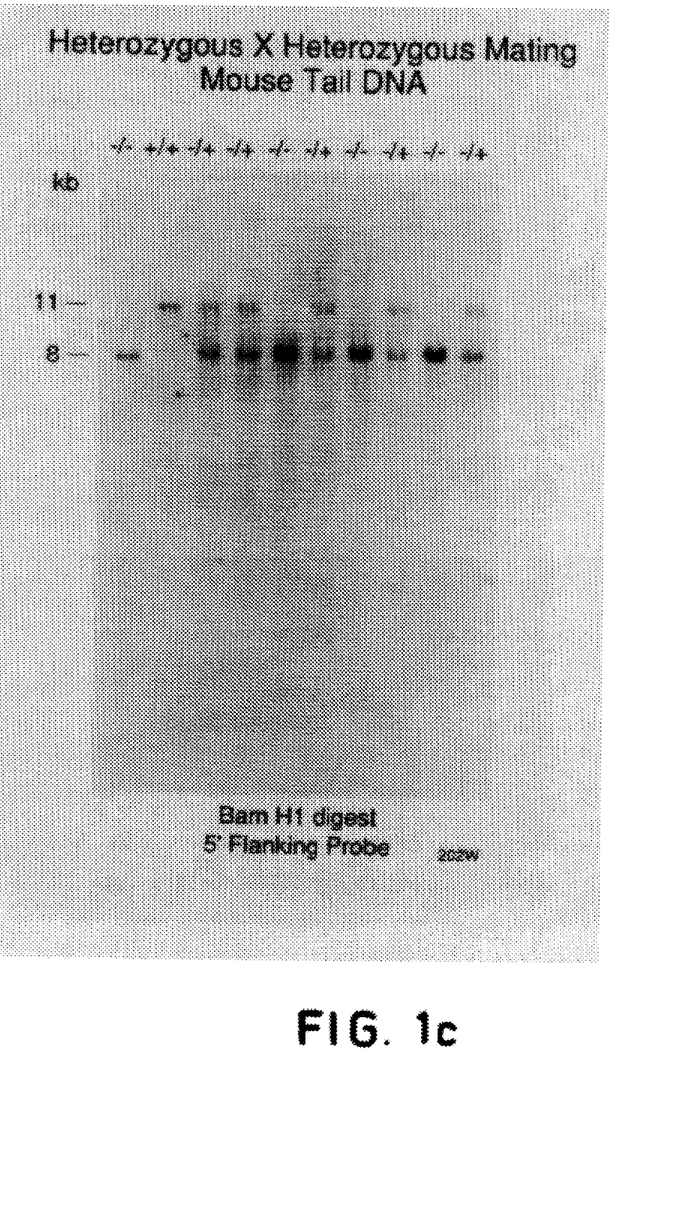
FIG. 1c shows Southern blot analysis of the genotypic identification of offspring resulting from inter-breeding of 32.3 derived heterozygous mice.
Figure 2A:
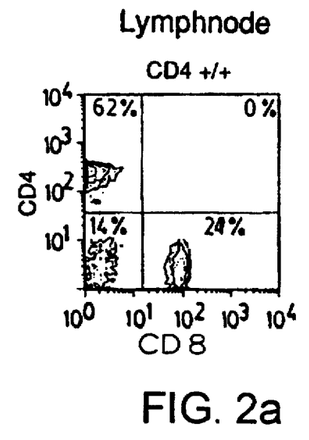
FIGS. 2a–2l show flow cytometric analyses of lymph node cells and thymocytes from 6 week old wild type (+/+) mice and mice heterozygous (+/−) and homozygous (−/−) for the 32.3 derived disrupted CD4 gene.
Figure 2B:
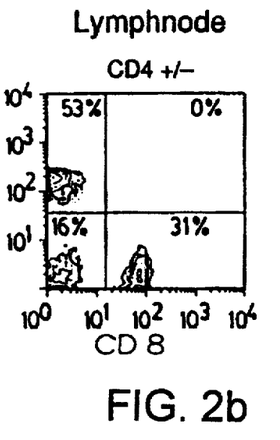
Figure 2C:
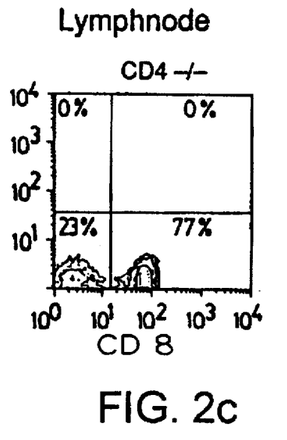
Figure 2D:
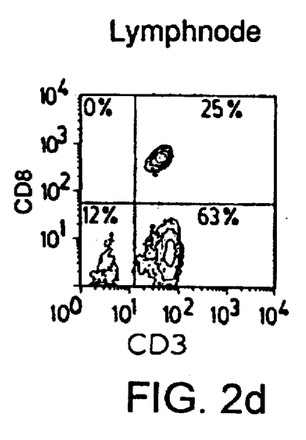
Figure 2E:
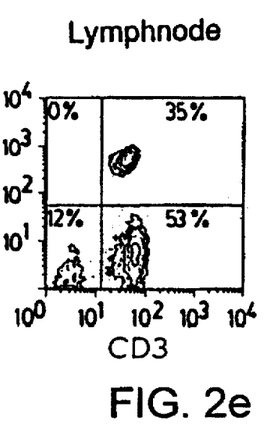
Figure 2F:
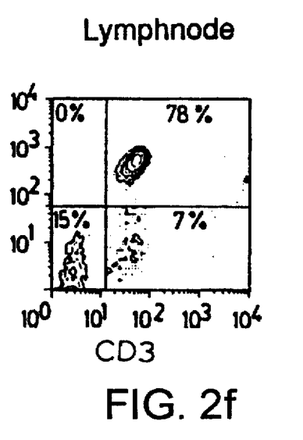
Figure 2G:
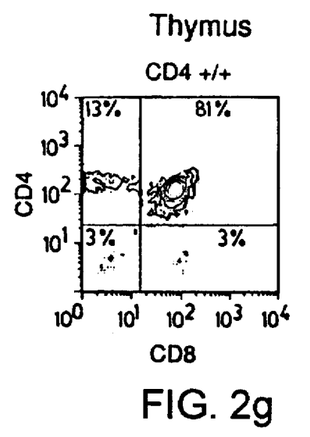
Figure 2H:
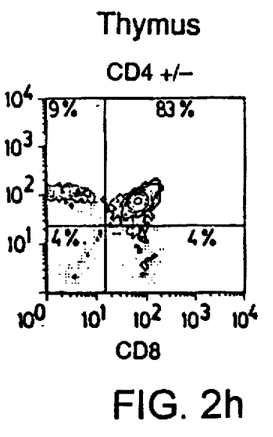
Figure 2I:
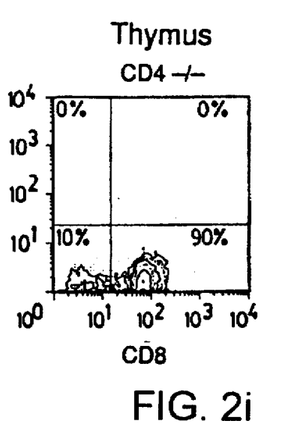
Figure 2J:
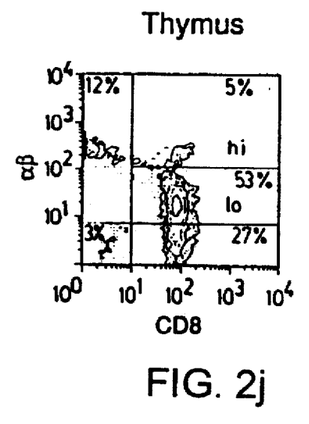
Figure 2K:
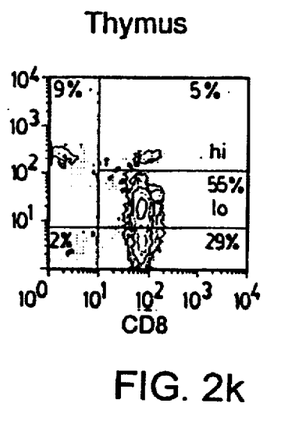
Figure 2L:
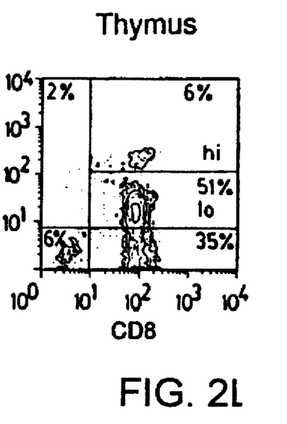

The CD4 molecule is a 55 kd cell surface glycoprotein found on thymocytes and a subpopulation of peripheral blood lymphocytes, and exists on the cell surface as a monomeric structure. The CD4 gene in the mouse is 26 kb long and has 10 exons and 9 introns[11]. For homologous recombination, a replacement-type vector was designed to create a mutant CD4 gene. As shown in FIG. 1a, this vector was a 2.8 kb genomic fragment (pML3T4Neo) containing exon 5 and exon 6. Exon 5, which encodes the V' region in the extra-cellular domain of the CD4 molecule, was disrupted by insertion of the bacterial neomycin phosphotransferase gene (neo) with its own polyadenylation signal and driven by the Herpes Simplex virus (HSV) thymidine kinase (tk) promoter with an upstream tandem repeat of the polyoma mutant enhancer region[8]. The neo cassette used contains the 1.2 kb XhoI-SalI fragment of plasmid pMCIPolA inserted in the SalI site created a previous KpnI site in exon V of the 2.8 kb genomic fragment of the CD4 gene. The neogene in this construct is driven by the HSV tk promoter with an upstream tandem repeat of the polyoma mutant enhancer region. The sizes of the BamHI, BglII and HindIII fragments hybridizing with the 5' flanking Exon IV probe and the neo probe are shown in FIG. 1a. This DNA construct was introduced into D3 ES cells by electroporation. Eight independent lines of ES cells with one of the alleles at the CD4 locus disrupted were generated (Table 1a). D3 embryonic stem cells from 129/sv mice were maintained in the undifferentiated state either by growth on feeder layer of mitomycin C treated primary embryonic fibroblasts or in culture medium supplemented with leukemia inhibitory factor. Electroporation of embryonic stem cells, selection of G 418 resistant colonies and PCR screening for homologous recombination were carried out according to Joyner et al[12]. A primer specific for the neo cassette within the HSV tk promoter, (5'-ATTCGCCAATGACAAGACGCTGG-3'), (SEQ ID NO:1) and another primer specific for the CD4 gene within exon IV and 5' of the targeting vector (5'-GAGGTTCGCCTTCGCAGTTTGAT-3') (SEQ ID NO:2) were used in the polymerase chain reaction. CD4 cDNA was used as the hybridization probe for the PCR screening. Homologous recombination (HR) was confirmed by genomic Southern blot hybridization. The average frequency of homologous recombination was about 1 in 2×10$^7$ electroporated cells or 1 in 300 G418-resistant clones. Southern blot analysis, using DNA of the CD4 gene flanking the region covered by the construct and the neogene as probes, confirmed the replacement of the endogenous CD4 gene by single copy insertions of the construct by homologous recombination (FIG. 1b). Six of the targeted clones were injected into pre-implantation embryos from C57B1/6J mice and mice with germline transmission representing four of the six independent clones were obtained (Table 1b). Chimeric mice were generated by injecting the targeted ES clones into three and a half day pre-implantation embryos derived from super-ovulated C57B1/6J females and transferring them into two and a half day pseudo-pregnant CD1 females. Germline transmission of the targeted CD4 alleles was assessed by breeding the chimeric males with (C57B1/6xDBA/2) F1 females and checking for the ES cell-derived agouti coat colour. Once the germline transmitters were identified, they were bred with C57B1/6J females. Complete transmitters are a result of sex conversion due to a high contribution of XY ES cells in an XX host. Heterozygous mice from three of these lines were interbred to obtain mice homozygous for the disrupted CD4 gene (FIG. 1c. Data from 39.2 and 58.8 derived mutant alleles not shown).

TABLE 1a

Electroporation with pML3T4Neo.16

| No. of cells electroporated | G418 resistant colonies tested (total colonies) | PCR+ colonies | HR confirmed by genomic southern blotting |
|---|---|---|---|
| $5 \times 10^7$ | 880 (1500) | 5 | 3 |
| $5 \times 10^7$ | 960 (2000) | 4 | 2 |
| $5 \times 10^7$ | 600 | 6 | 3 |

TABLE 1b

Germ-line Transmission of Targeted CD4 Alleles

| Cell line | Male chimaera | Female chimaera | Germline transmission |
|---|---|---|---|
| D3 | 17 | 4 | 8 3-complete 5-partial |
| 34.4 | 15 | 5 | None |
| 32.3 | 20 | 9 | 14 1-complete 13-partial |
| 39.2 | 10 | 5 | 3 (4 tested) |
| 44a.8 | 4 | 2 | Not done |
| 58.8 | 2 | 4 | 1 |
| 59.3 | 1 | 1 | 1 |

Phenotypic Analysis

Homozygous mice from matings between mice, heterozygous for 32.3 and 39.2 derived mutant CD4 alleles were apparently healthy, fertile and indistinguishable from heterozygous or wild type littermates on gross physical inspection. Of particular interest was the lack of alteration in the size of the lymphoid organs (i.e. thymus, lymph nodes, spleen) and the apparently normal development of the hemopoietic system. The number of cells in the lymphoid organs were similar to those in heterozygous or wild type mice. The number of T and B cells, as identified by antibodies specific for Thy-1.2 and immunoglobulin M (IgM), respectively in lymph nodes of these mice were found to be normal by flow cytometric analysis (data not shown). In addition, myeloid differentiation, as measured by colony forming units in culture (CFU-C) of bone-marrow cells was also unaltered (data not shown). Mice homozygous for the disrupted CD4 gene expressed normal levels of MHC class I and II proteins as determined by florescence cell activating staining (data not shown). "Normal" here refers to that level of expression found in wild type mice.

As expected, surface expression of CD4 was not detected on thymocytes (FIGS. 2g–2l) or lymph node cells (FIGS. 2a–2f) from mice homozygous for the 32.3 and 39.2 derived mutant CD4 alleles (FIG. 2). Single cell suspensions from thymus and lymph nodes of 6-week old mice were made and $2-5 \times 10^5$ cells were stained with monoclonal antibodies for 45 minutes at 4° C. in 100 μl phosphate-buffered saline containing 1% bovine serum albumin and 0.1% sodium azide. Cells were then washed and analyzed for double-colour flow cytometric analysis on a FACScan® (Becton Dickinson, Inc.). Monoclonal antibodies used were anti-Lyt-2 (53-6.7, Becton Dickinson, Inc.), anti-L3T4 (GK1.5, Becton Dickinson, Inc.), anti-CD3 (145-2C11, PharMingen, Inc.), anti-αβ TcR (H57-597, PharMingen). Surface expression of CD4 on lymph node cells from heterozygous mice is slightly reduced suggesting that a gene dosage effect may exist. Staining of the thymocytes in the CD4 deficient homozygous mice showed that $CD8^+$ cells are present in normal numbers in the thymus but have expanded in the periphery to apparently occupy the compartment that would otherwise have been occupied by $CD4^+8^-$ cells. Also present in the lymph nodes are some cells that are $TcR_{\alpha\beta}^+CD4^-8^-$. The functional significance of this population is being investigated. Analysis using antibodies against CD3 and $TcR_{\alpha\beta}$ showed that the expression of these molecules is normal on thymocytes of the mutant mice. There is no significant difference in the proportion of cells with high and low levels of $TcR_{\alpha\beta}$ on the surface, between the wild type mice, heterozygous mice and the homozygous mutant mice. This suggests normal maturation of the $CD8^+$ T cells as far as the expression pattern of $TcR_{\alpha\beta}$ on the thymocytes is concerned. These results demonstrate that the expression of CD4 on the surface of the progenitor cells and on the double positive thymocytes is not required for the normal development of $CD4^-8^+$ T cells.

IL-2 Release

Murine helper T cells are Class II MHC restricted and of the $TcR_{\alpha\beta}^+ CD4^+8^-$ phenotype. This population was absent from the thymus and lymph nodes of mice homozygous for the 32.3 and 39.2 derived disrupted gene. An investigation was made to determine whether IL-2 secretion by T cells in response to allo-antigens was abnormal as a result of absence of the $TcR_{\alpha\beta}^+CD4^+CD8^-$ subpopulation. Results demonstrate that in mice homozygous for the disrupted CD4 gene, the ability of the responder spleen cells to produce IL-2 was greatly reduced but there were cells other than $CD4^+$ cells that were able to produce IL-2 in response to alloantigens (data not shown). The precursor frequency of the IL-2 producing cells in these mice ($H-2^b$) against $H-2^q$ determinants was ten-fold less than that in heterozygous mice (Table 2a). $3 \times 10^5$ irradiated stimulator cells ($H-2^q$) were cultured in 0.2 ml with varying number of responder cells ($H-2^b$), that were heterozygous (+/−) or homozygous (−/−) for the 32.3 derived mutant CD4 allele (eight replicates for each responding cell number). After 3 days of incubation, 100 μl of the supernatant from each well was assayed for IL-2 activity using the CTLL assay[13]. Background IL-2 release was measured in replicate wells that received only stimulator cells. The threshold for a positive response was set as 3SD above the mean background value. The fraction of negative cultures was plotted against the number of responder cells. Frequencies, 95% confidence limits and $\chi^2$ values for a fit to limiting dilution theory were calculated according to the Porter and Berry method[14]. In order to determine whether IL-2 was being secreted in response to class I or class II MHC differences, spleen cells from these mice were stimulated with allogenic cells which differed in class I MHC ($H-2^{bm1}$), class II MHC ($H-2^{bm12}$) or both ($H-2^r$). Primary bulk MLR cultures were set up.

Figure 3A:
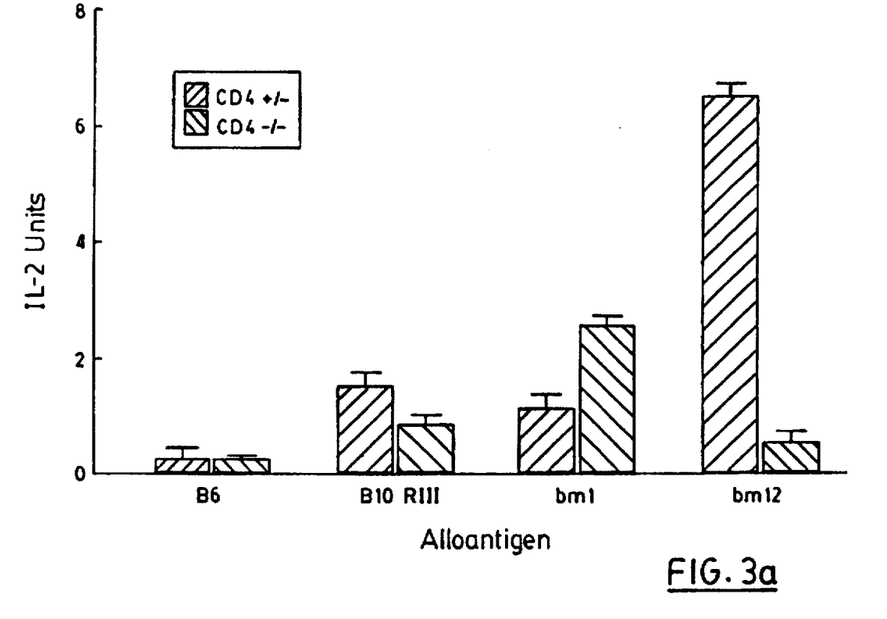
FIG. 3a shows CTLL assay results for helper function. IL-2 activity is measured against MHC class restriction in mixed lymphocyte reaction.

Responder cells were spleen cells from adult (6–8 week old) mice heterozygous (+/−) and homozygous (−/−) for the 32.3 derived mutant allele. These mice were of haplotype H-2$^b$. The stimulator cells were from mouse strains C57B1/6J (H-2$^b$), B10RIII(71NS)(H-2$^r$), C57B1/6bm1 (H-2$^{bm1}$) or C57B1/6bm12 (H-2$^{bm12}$). $2 \times 10^7$ responder cells were cultured with $2 \times 10^7$ irradiated (2000cGy) stimulator cells in 20 ml of culture medium. On day three IL-2 activity in 100 μl of supernatant was determined using the CTLL-assay. The amount of IL-2 secreted by homozygous mice in the responses against class II differences was much lower than that secreted by heterozygous mice (FIG. 3a). Higher amounts of IL-2 were found in homozygous mice in responses against class I MHC difference but this could be accounted for, by the increased number of CD8$^+$ cells in these mice.

B cell Function

Figure 3B:
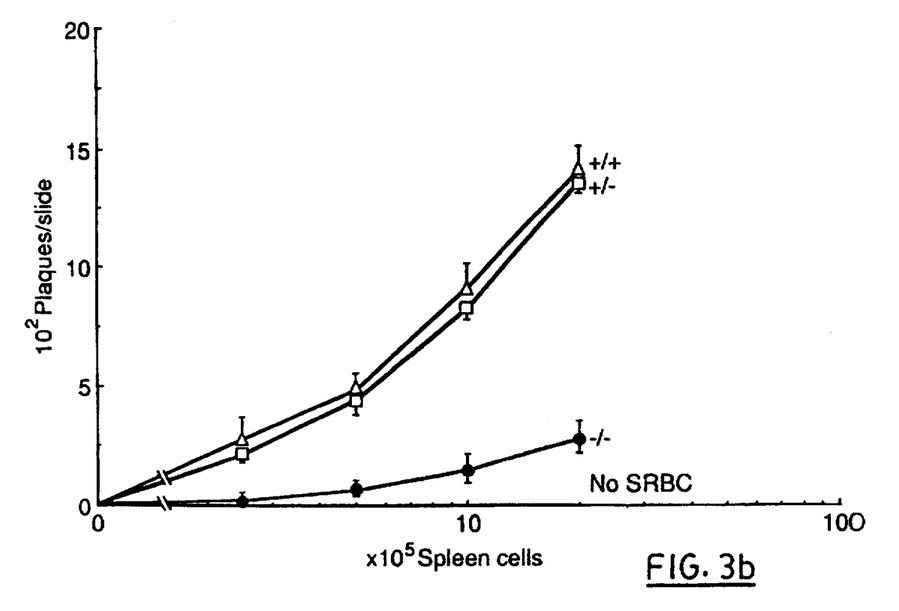
FIG. 3b shows anti-sheep erythrocyte (SRBC) specific plasma cell enumeration.
Figure 4A:
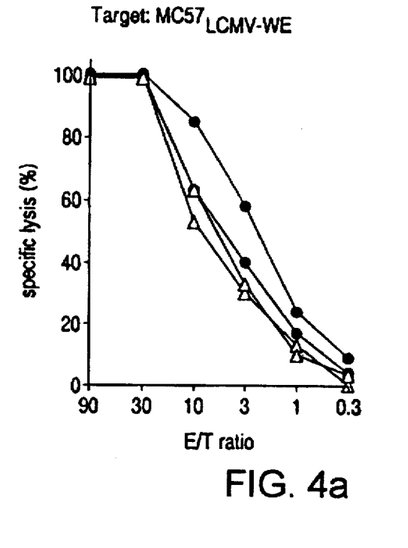
FIGS. 4A–4D shows cytotoxic activities of T cells from spleens of mice heterozygous (+/−) and homozygous (−/−) for the 32.3 derived CD4 allele.
Figure 4B:
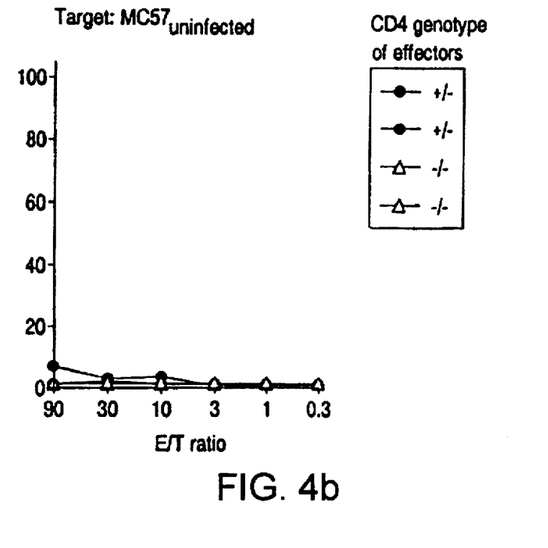
Figure 4C:
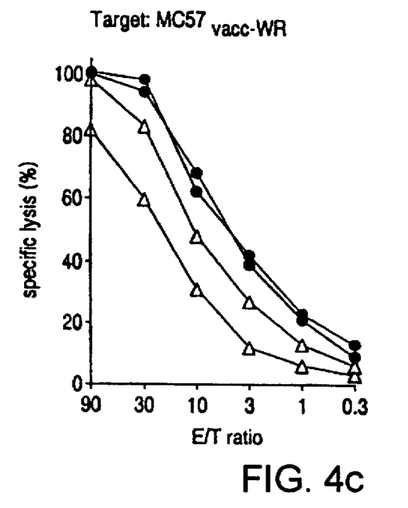
Figure 4D:
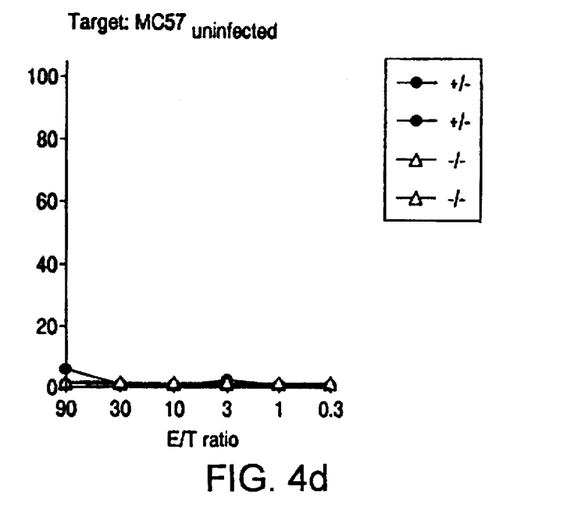

The ability of the mouse which lacked CD4 expression to mount an effective anti-sheep erythrocyte (anti-SRBC) response was tested. Six days after intra-peritoneal injection of sheep erythrocytes, mice homozygous for the mutant CD4 allele showed markedly reduced amounts of anti-SRBC antibodies in their sera (Table 2b). Furthermore, in vitro plaque-forming assays demonstrated that the spleens of homozygous mice had markedly reduced frequencies of plasma cells producing anti-SRBC antibody (FIG. 3b).

In order to exclude any intrinsic defect in the B cells, the B cells were tested for their ability to respond to lipopolysaccharide (LPS), a B cell mitogen. Cells from the CD4 defective mice were found to respond as well as cells from mice, heterozygous for the disrupted CD4 gene, or wild type mice (data not shown). This result shows that the inability of the mice without CD4 expression to mount a normal B cell response against SRBC is not due to any defect in the B cells themselves but rather the incompetence of the T cells to provide "help".

TABLE 2a

Precursor Frequency Estimates of IL-2 Producing Cells in Anti-SWR (H-2$^q$) Responses

| CD4 | Freq/10$^6$ | 95% Confidence Limits | $\chi^2$ |
| --- | --- | --- | --- |
| +/− | 212 | 124–359 | 3.92 |
| −/− | 20 | 11–32 | 1.12 |

TABLE 2b

Anti-Sheep Erythrocyte Response

| | CD4+/+ | CD4+/− | CD4−/− |
| --- | --- | --- | --- |
| | | Antibody titre | |
| Pre-immune | <1/20 | <1/20 | <1/20 |
| 5 days post-SRBC inj. | 1/1280 | 1/1280 | 1/80 |

Cytotoxic Activity

Murine cytotoxic T cells are considered to be exclusively TcR$_{\alpha\beta}^+$ CD4$^-$8$^+$. In order to test whether this population functioned normally and could mount a cytotoxic response against viruses, these mice (H-2$^b$) were infected intravenously with either lymphocytic choriomeningitis virus (LCMV) or Vaccinia virus. The cytotoxic activity of the spleen cells against these viruses was measured in a standard chromium release assay using virally infected cells as targets. Mice homozygous for the 32.3 derived mutant allele generated cytolytic T cell activity against both viruses that was either comparable with or within a 2–3 fold range of that generated by wild type and heterozygous mice (FIGS. 4a–4d). As shown in FIGS. 4A–4D, the anti-viral cytolytic activity of T cells was tested in a standard $^{51}$Cr release assay using MC57G(H-2$^b$) and natural killer cell sensitive YAC as target cells. Virus infected targets were prepared by incubating the cells with the virus and the Na$^{51}$CrO$_4$ for 1 h. at 37° C. The target cells were washed three times with medium containing fetal calf serum (FCS). 2 adult mice were infected intravenously with either LCMV or Vaccinia virus. Cytotoxicity assays were carried out 6 days after injection of $2 \times 10^6$ plaque forming units (PFU) of Vaccinia Virus and 8 days after injection of $2 \times 10^2$ PFU of the LCMV strains. Single cell suspensions of spleen cells were assayed in duplicate. Effector and target cells ($1 \times 10^4$) were added in a total volume of 0.20 ml to round-bottomed 96-well plates to yield effector to target ratios of 90:1, 30:1, 10:1, 3:1, 1:1, and 0.3:1. After mixing, the plates were centrifuged at 400 g for 5 minutes and incubated at 37° C. in air containing 5% CO$_2$. The percentage specific $^{51}$Cr release was calculated as (experimental release-spontaneous release)/(total release-spontaneous release)×100.

The invention provides a means for investigating the role of CD4 in lymphocyte development and function by using CD4 defective mice generated through homologous recombination in ES cells. The data show that the absence of CD4 expression in the mutant mice results in apparently normal hemopoiesis. It has previously been shown that CD4 was expressed at a low level on the surface of an early hemopoietic progenitor cell and on the surface of the thymocyte precursors. The present data have shown conclusively that the presence of CD4 on these cells is not required for either haemopoiesis or lymphopoiesis. Normal levels of myeloid and lymphoid cells can be found in the mice of the invention.

The data also shows that the absence of CD4 expression in the mutant mice greatly reduced the development of class II MHC restricted helper T cells. Recognition of the appropriate class II MHC molecule by the TcR has been shown to be decisive for positive selection of class II MHC-restricted helper T cells. The invention confirms that the presence of the CD4 molecule on the surface of the thymocytes is necessary for the development and positive selection of functional class II MHC-restricted T cells. While the TcR appears to recognize the polymorphic domains of the class II MHC molecule, CD4 probably interacts with the non-polymorphic domains of class II MHC molecule. The lack of either one of these interactions results in the block of the development of class II MHC-restricted helper T cells. In addition, the results demonstrated that the expression of CD4 on the CD4$^+$8$^+$ thymocyte is not obligatory for the selection of CD4$^-$8$^+$ cells. Conversely, it has been shown recently that surface expression of CD8 on the immature thymocytes is not obligatory for the selection of CD4$^+$8$^-$ cells[15].

The role of CD4 in thymic selection of the T cell repertoire has been previously investigated using monoclonal antibodies against the CD4 molecule[16,17]. Although the use of anti-CD4 monoclonal antibodies has provided some insight into the function of the CD4 molecule in thymic selection, the conclusions are limited because of disadvantages in using monoclonal antibodies. The present approach is particularly useful to study the effect of the lack of a particular subpopulation on long term development of the immune system and to study the compensatory potential that the immune system may possess.

The CD4$^+$ helper T cells also play an important role in regulating the immune responses. These cells have been shown to regulate antibody production, and the inability of the CD4 deficient mice to mount an efficient anti-SRBC B-cell response confirms this data. Whether and how much T help is needed for the induction of a cytotoxic T cell response, depends on the virus studied. Some in vivo experiments suggest a mandatory role for T help, while others show that T help is not necessary for Class I MHC-restricted T-cell responses in vivo. The present invention demonstrates definitively the ability of CD4⁻8⁻ T cells to mount an effective anti-viral cytotoxic response in the absence of CD4⁺ helper T cells.

Several researchers have suggested that CD4⁻8⁺ cells may be the source of "help" mediated through lymphokine production. The present invention shows that the CD8⁺ cells that develop in the absence of CD4 can secrete IL-2 in response to class I MHC difference and may be a potential source of "help". On the other hand, double negative $TcR_{\gamma\delta}^+$ or $TcR_{\alpha\beta}^+$ cells may be responsible for providing the help. Experiments with allogeneic bone marrow chimeras have provided evidence that help for the cytotoxic T cells is mediated by interleukins independent of cell-cell contact and thus differs from T help for B cells[18]. The finding of a relatively normal CTL response against viruses in the absence of CD4⁺ helper cells clearly has important implications for our understanding of the role of CD4⁺ cells in in vivo immune reactions.

The mutant mouse strain of the invention has not only provided a model to study ontogeny and functions of the immune system, but also a model for the immunological consequences of diseases such as AIDS, where the CD4⁺ cells are reduced or absent. These mice or other mammals should also provide valuable information about the role of the CD4⁺ cells in fighting infections, in tumor and allograft rejection, in the pathogenesis of graft versus host disease and in autoimmune diseases, particularly ones in which autoantibodies are generated.

Deposits

ES cell line 32.3 with the disrupted CD4 gene as shown in FIG. 1a has been deposited in the American Type Culture Collection, Rockville, Md., and given ATCC Accession No. CRL 11114.

REFERENCES

1. Cobbold, S. P., Jayasuriya, A., Nash, A., Prospero, T. D. and Waldmann, H. Nature 312, 548–551 (1984)
2. Cobbold, S. P. and Waldmann, H. Transplantation 41, 634–639 (1986)
3. Leist, T. P., Cobbold, S. P., Waldmann, H., Aguet, M. and Zinkernagel, R. M. J. Immunol 138, 2278–2281 (1987)
4. Moskophidis, D., Cobbold, S. P., Waldmann, H. and Lehmann-Grube, F. J. Virol. 61, 1867–1874 (1987)
5. Evans, M. J. and Kaufman, M. H. Nature 22, 154–156 (1981)
6. Martin, G. R. Proc. Natn. Acad. Sci. USA, 78, 7634–7638 (1981)
7. Smithies, O., Gregg, R. G., Boggs, S. S., Koralewski, M. A. and Kucherlapati, R. S. Nature 317, 230–234 (1985)
8. Thomas, K. R. and Capecchi, M. R. Cell 51, 503–512 (1987)
9. Gossler, A., Doetschman, T., Korn, R., Serfling, E. and Kemler, R. Proc. Natn. Acad. Sci. 83, 9065–9069 (1986)
10. Robertson, E., Bradley, A., Kuehn, M. and Evans, M. Nature 323, 445–447 (1986)
11. Gorman, S. D., Tourville, B. and Parnes, J. R. Proc. Natn. Acad. Sci. USA, 84, 7644–7648 (1987)
12. Joyner, A. L., Skarnes, W. C. and Rossant, J. Nature 338, 153–156 (1989)
13. Gillis, S., Ferm, M. M. Ou, W. and Smith, K. A. J. Immunol. 120, 2027–2032 (1978)
14. Porter, E. H. and Berry, R. J. Br. J. Cancer. 17, 583 (1964)
15. Fung-Leung, W. P. et al, Cell, 65, 443–449 (1991)
16. Fowlkes, B. J., Schwartz, R. H. and Pardoll, D. M. Nature 334, 620–623 (1988)
17. MacDonald, H. R., Hengartner, H. and Pedrazzini, T. Nature 335, 174–176 (1988)
18. Zinkernagel, R. M., Ruedi, E., Althage, A., Hengartner, H. and Reimann, G. J. Exp. Med. 168, 1187–1192 (1988)

I claim:

1. A mouse homozygous for a disrupted CD4 gene, wherein the CD4 gene is disrupted by a selectable marker sequence, wherein said disruption prevents expression of the CD4 cell surface antigen, and wherein said mouse has peripheral blood $CD8^+$ thymocytes and expresses class I MHC antigens on the surface of its cells.

2. The mouse as claimed in claim 1, wherein said disruption is the integration of a DNA fragment comprising a selected exon or selected exons of said CD4 gene, wherein a marker for neomycin resistance has been inserted into said exon or one of said exons.

3. The mouse as claimed in claim 2, wherein said disruption is the integration of a 2.8 kb DNA fragment containing exons 5 and 6 of said gene, wherein the marker for neomycin resistance has been inserted into the SalI site of exon 5.

4. The mouse as claimed in claim 3, wherein said DNA fragment is introduced into D3 embryonic stem cells by electroporation, and wherein a resulting neomycin resistant D3 cell, identified by the polymerase chain reaction to have integrated said fragment by homologous recombination into its genome, is introduced into said mouse or an ancestor of said mouse at an embryonic stage.

5. Embryonic stem cell line ATCC Accession No. 11114, wherein said cell line comprises a disrupted CD4 gene.

* * * * *

UNITED STATES PATENT AND TRADEMARK OFFICE
CERTIFICATE OF CORRECTION

PATENT NO.  : 5,698,765
DATED       : December 16, 1997
INVENTOR(S) : TAK W. MAK It is certified that error appears in the above-identified patent and that said Letters Patent is hereby corrected as shown below:

Column 1, line 7, please delete "mice" and insert --mouse--;

Column 2, line 34, please delete "SaII" and insert --SalI--;

Column 2, line 36, please delete "neogene" and insert in its place --neo gene--;

Column 2, line 63, please delete "neogene" and insert in its place --neo gene--; and Column 7, line 9, please delete "CD4⁻8⁻" and insert in its place --CD4⁻8⁺--.

Signed and Sealed this

Second Day of May, 2000

Q. TODD DICKINSON

*Attest:*

*Attesting Officer*   *Director of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 23 base pairs
( B ) TYPE: nucleic acid
( C ) STRANDEDNESS: single stranded
( D ) TOPOLOGY: linear ( x i ) SEQUENCE DESCRIPTION: SEQ ID NO:1:

ATTCGCCAAT GACAAGACGC TGG  23

( 2 ) INFORMATION FOR SEQ ID NO:2:

( i ) SEQUENCE CHARACTERISTICS:
( A ) LENGTH: 23 base pairs
( B ) TYPE: nucleic acid
( C ) STRANDEDNESS: single stranded
( D ) TOPOLOGY: linear (xi) SEQUENCE DESCRIPTION: SEQ ID NO:2:

GAGGTTCGCC TTCGCAGTTT GAT    23